(12) United States Patent
Rust et al.

(10) Patent No.: US 7,815,656 B2
(45) Date of Patent: Oct. 19, 2010

(54) METHOD FOR ENDOVASCULAR BYPASS STENT GRAFT DELIVERY

(75) Inventors: Matthew Rust, Santa Rosa, CA (US); Prema Ganesan, San Francisco, CA (US); Curtis Hanson, San Diego, CA (US); Jack Chu, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 647 days.

(21) Appl. No.: 11/464,036

(22) Filed: Aug. 11, 2006

(65) Prior Publication Data

US 2007/0203565 A1   Aug. 30, 2007

Related U.S. Application Data

(62) Division of application No. 10/891,397, filed on Jul. 14, 2004, now abandoned.

(60) Provisional application No. 60/574,503, filed on May 26, 2004.

(51) Int. Cl.
*A61B 17/08* (2006.01)
(52) U.S. Cl. .................................. 606/153; 623/1.35
(58) Field of Classification Search ............... 128/898; 606/108, 184, 153, 155; 623/1.11, 1.23, 623/1.36, 2.11
See application file for complete search history.

(56) References Cited

U.S. PATENT DOCUMENTS

| | | | |
|---|---|---|---|
| 5,755,775 A | 5/1998 | Trerotola et al. | |
| 5,797,920 A | 8/1998 | Kim | |
| 5,797,935 A | 8/1998 | Barath | |
| 5,830,222 A | 11/1998 | Makower | |
| 6,004,330 A | 12/1999 | Middleman et al. | |
| 6,026,814 A | 2/2000 | Lafontaine et al. | |
| 6,035,856 A | 3/2000 | Lafontaine et al. | |
| 6,068,638 A | 5/2000 | Makower | |
| 6,071,292 A | 6/2000 | Makower et al. | |
| 6,159,225 A | 12/2000 | Makower | |
| 6,190,353 B1 | 2/2001 | Makower | |
| 6,231,587 B1 | 5/2001 | Makower | |
| 6,253,769 B1 | 7/2001 | Lafontaine et al. | |
| 6,283,951 B1 | 9/2001 | Flaherty et al. | |
| 6,283,983 B1 | 9/2001 | Makower et al. | |
| 6,290,728 B1 | 9/2001 | Phelps et al. | |
| 6,302,875 B1 | 10/2001 | Makower et al. | |
| 6,330,884 B1 | 12/2001 | Kim | |

(Continued)

FOREIGN PATENT DOCUMENTS

WO    WO01/10341    2/2001

*Primary Examiner*—Anhtuan T Nguyen
*Assistant Examiner*—Tuan V Nguyen

(57) ABSTRACT

The invention provides a method of providing an endovascular bypass. The method includes the steps of inserting an elastic needle carrying a guidewire adjacent an ostium via a catheter and extending the needle through a branch vessel wall. The method continues by extending the needle through the extravascular space and inserting the needle through a main vessel wall to create an opening. The needle is retracted, leaving the guidewire in place. A bypass stent graft is inserted along the guidewire to provide a pathway between the branch vessel and the main vessel, and the inserted bypass stent graft is expanded. The branch vessel is occluded between the ostium of the bypass stent graft and the main vessel, and a main stent graft is inserted in the main vessel proximate the opening in the main vessel wall.

17 Claims, 10 Drawing Sheets

U.S. PATENT DOCUMENTS

| | | |
|---|---|---|
| 6,352,543 B1 | 3/2002 | Cole |
| 6,375,615 B1 | 4/2002 | Flaherty et al. |
| 6,428,565 B1 | 8/2002 | Wisselink |
| 6,432,127 B1 | 8/2002 | Kim et al. |
| 6,491,707 B2 | 12/2002 | Makower et al. |
| 6,508,824 B1 | 1/2003 | Flaherty et al. |
| 6,517,574 B1 | 2/2003 | Chuter |
| 6,544,230 B1 | 4/2003 | Flaherty et al. |
| 6,561,998 B1 | 5/2003 | Roth et al. |
| 6,569,145 B1 | 5/2003 | Shmulewitz et al. |
| 6,579,311 B1 | 6/2003 | Makower |
| 6,592,559 B1 | 7/2003 | Pakter et al. |
| 6,599,302 B2 * | 7/2003 | Houser et al. ............... 606/153 |
| 6,602,241 B2 | 8/2003 | Makower et al. |
| 6,616,675 B1 | 9/2003 | Evard et al. |
| 6,655,386 B1 | 12/2003 | Makower et al. |
| 6,660,024 B1 | 12/2003 | Flaherty et al. |
| 6,726,677 B1 | 4/2004 | Flaherty et al. |
| 6,843,795 B1 | 1/2005 | Houser et al. |
| 7,144,421 B2 * | 12/2006 | Carpenter et al. .......... 623/1.31 |
| 2001/0010007 A1 * | 7/2001 | Bachinski et al. ............ 606/153 |
| 2002/0045928 A1 | 4/2002 | Boekstegers |
| 2002/0099394 A1 | 7/2002 | Houser et al. |

* cited by examiner

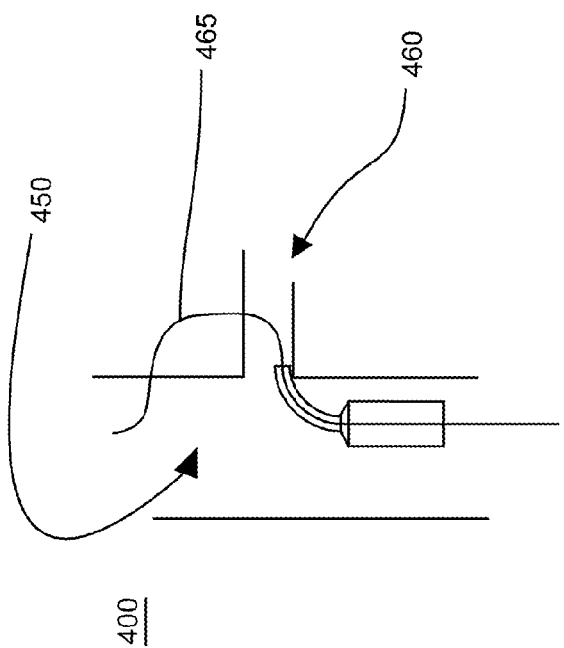
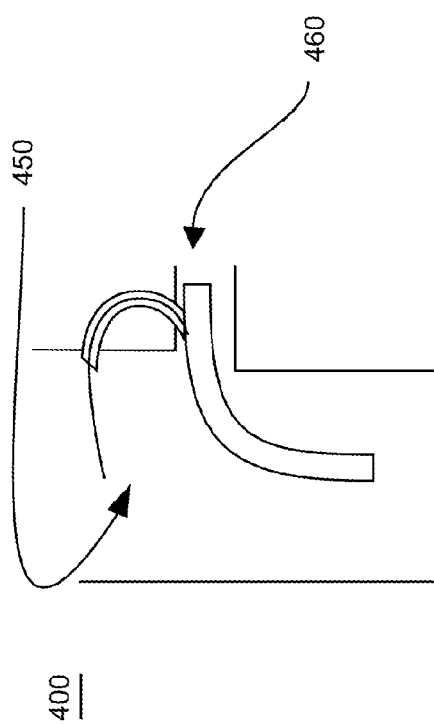
FIG. 4B
FIG. 4A

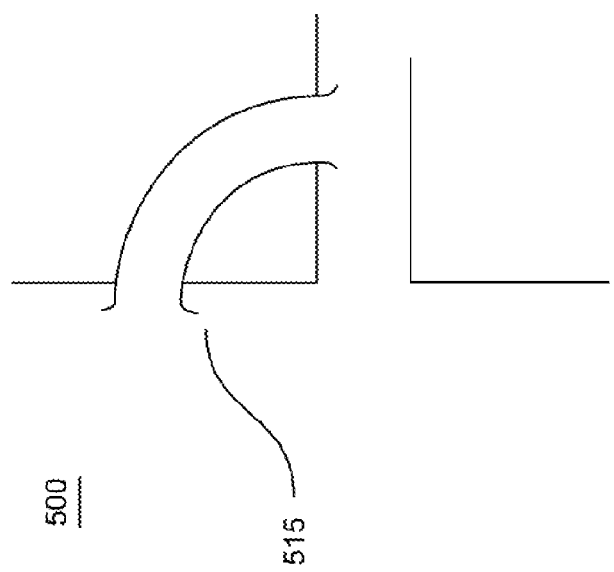
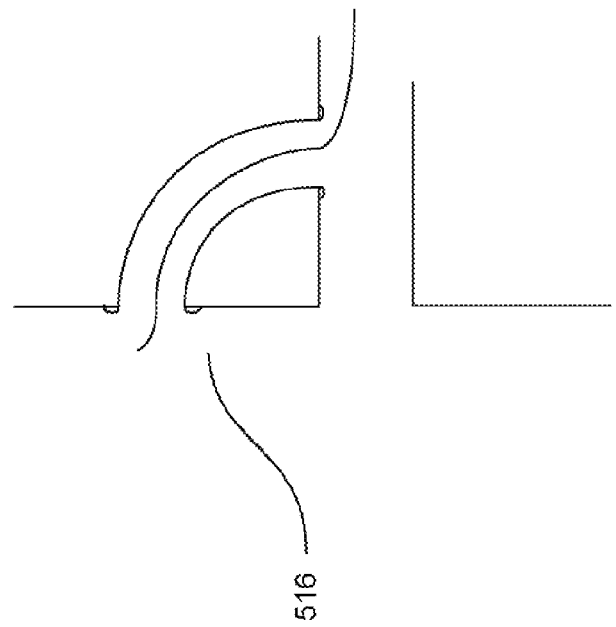

METHOD FOR ENDOVASCULAR BYPASS STENT GRAFT DELIVERY

RELATED APPLICATIONS

This application is a divisional application of U.S. patent application Ser. No. 10/891,397 filed Jul. 14, 2004, now abandoned, and claims the benefit of that application. The entirety of that application is incorporated herein by reference. That application claimed the benefit of U.S. Provisional Application 60/574,503 filed on May 26, 2004.

TECHNICAL FIELD

This invention relates generally to biomedical devices that are used for treating vascular conditions. More specifically, the invention relates to a method for endovascular bypass stent graft delivery.

BACKGROUND OF THE INVENTION

Stents are generally cylindrical-shaped devices that are radially expandable to hold open a segment of a vessel or other anatomical lumen after implantation into the body lumen.

Various types of stents are in use, including expandable and self-expanding stents. Expandable stents generally are conveyed to the area to be treated on balloon catheters or other expandable devices. For insertion, the stent is positioned in a compressed configuration along the delivery device, for example crimped onto a balloon that is folded or otherwise wrapped about a guidewire that is part of the delivery device. After the stent is positioned across the lesion, it is expanded by the delivery device, causing the diameter to expand. For a self-expanding stent, commonly a sheath is retracted, allowing expansion of the stent.

Stents may be used in conjunction with a graft. When the graft is used to deliver drugs or other therapeutic agents for medical therapeutic applications, 100% coverage of the portion of the vessel in direct contact with the graft is possible. The graft component of a stent graft may also aid in minimizing thrombosis, preventing embolic events, and minimizing contact between the fissured plaque and the hematological elements in the bloodstream.

In addition, the graft component makes the device suitable for use in treating aneurysms. An aneurysm is a bulge or sac that forms in the wall of a blood vessel. The force of normal blood pressure in the aneurysm may cause the vessel to rupture. Aneurysms result from many causes that weaken the vessel wall, including but not limited to heredity, trauma, or disease.

A number of methods and devices have been developed for treating aneurysms. A standard treatment is surgery, which is performed to bypass the section of the vessel where the aneurysm has formed. Some patients are not good candidates for such open surgery, and, due to the highly invasive nature of the open procedure, other patients may not wish to undergo the treatment.

An alternative treatment is a technique known as endovascular stent grafting. In this procedure, a stent graft is placed inside the vessel affected by the aneurysm to bypass the weakened vessel wall, thereby preventing rupture of the aneurysm. Like stents, stent grafts are delivered to the area to be treated using balloon catheters or other expandable devices and may deliver one or more therapeutic agents.

Placing stent grafts at the ostia of vessels has been difficult due to placement restrictions—placing a stent graft at an ostium requires that the stent graft be close to but not overlapping the ostium to maintain the desired blood flow between the main vessel and a branch vessel. Another approach is to provide a fenestration in the side of a graft at the branching ostium, in some instances, a branching tube to seal to the branch has been proposed. An exemplary approach is disclosed by Wisselink in U.S. Pat. No. 6,428,565. However, the Wisselink reference requires customizing the stent graft to correspond to the vessel anatomy ensuring the seal between the graft devices.

Therefore, it would be desirable to have a stent graft system that overcomes the aforementioned and other disadvantages.

SUMMARY OF THE INVENTION

One aspect according to the invention is a method of providing an endovascular bypass. The method includes inserting an elastic, e.g. shape-memory, needle adjacent an ostium via a catheter and extending the needle through a branch vessel wall. The needle is extended through an extravascular space and through a main vessel wall to create an opening. A guidewire is delivered via the needle. The needle is retracted, leaving the guidewire in place, and a bypass stent graft is inserted along the guidewire through the extravascular space between the branch vessel and the main vessel. The bypass stent graft is expanded and the branch vessel occluded between the opening of the bypass stent graft in the branch vessel and the main vessel. The method further includes inserting a main vessel stent graft in the main vessel proximate the opening of the bypass stent graft into the main vessel wall.

Another aspect according to the invention provides a system for treating an ostial aneurysm. The system includes a catheter including a retractable elastic needle carried within the catheter and covered with a sheath, wherein when the needle is positioned adjacent the ostium in a branch vessel, the needle deploys into a predetermined shape and punctures through a sidewall of the branch vessel through the extravascular space and through a sidewall of the main vessel, a guidewire is delivered via the needle, and the needle is retracted to allow placement of a bypass stent graft.

Yet another aspect according to the invention provides a system for treating a vascular condition. The system includes a catheter, a stent graft, and an elastic needle releasably carrying a guidewire disposed within the needle.

The aforementioned and other features and advantages in embodiments according to the invention will become further apparent from the following detailed description embodiments, read in conjunction with the accompanying drawings.

BRIEF DESCRIPTION OF THE DRAWINGS

FIGS. 4A, 4B, 4C, 4D, 4E and 4F are schematic cross sectional views of a vascular structure, illustrating in situ the steps of the method described in FIGS. 1A, 1B, 1C, and 1D;

FIGS. 5A and 5B are schematic cross sectional views of other embodiments of stent graft assemblies, in accordance with the present invention;

DETAILED DESCRIPTION

Figure 1:
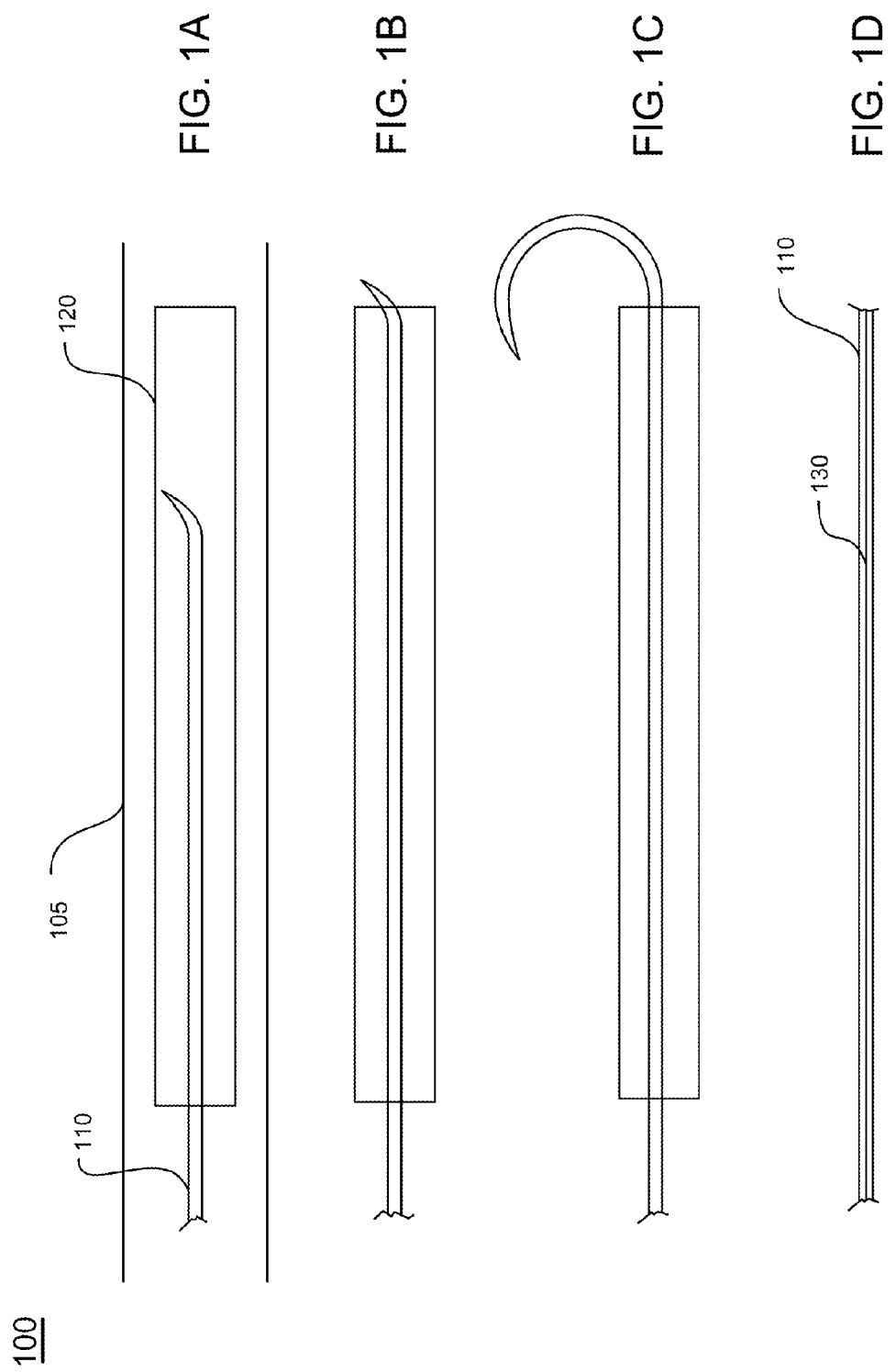
FIGS. 1A, 1B, 1C, and 1D are views of one embodiment of a needle assembly, in accordance with the present invention.

One embodiment of the invention comprises a needle system 100 as illustrated at FIGS. 1A, 1B, 1C and 1D. The system may be used to treat a vascular condition. For example, needle system 100 may be used to treat an ostial encroaching aneurysm. FIG. 1A illustrates needle system 100 prior to deployment. Needle system 100 includes needle 110 carried within a retractable sheath 120. Needle 110 and sheath 120 are delivered through a catheter 105, which is shown only in FIG. 1A.

Needle 110 is a curved needle comprising a shape-memory material. In one embodiment, needle 110 comprises nitinol. In other embodiments, needle 110 comprises tantalum, MP35N alloy, platinum, titanium, a chromium-based alloy, a suitable biocompatible alloy, a suitable biocompatible polymer, or combinations thereof. Prior to deployment, needle 110 is restrained in a substantially straight configuration by sheath 120.

FIG. 1B illustrates needle system 100 during deployment. As shown, while sheath 120 is held stationary, the needle is extended, allowing needle 110 to partially resume its preset shape. FIG. 1C illustrates needle system 100 in a deployed configuration. Needle 110 has assumed its preset shape-memory configuration. In one embodiment, the preset shape is an arc or curved shape.

Needle 110 is hollow with the internal diameter sized to carry a guidewire 130 within the needle, as seen in FIG. 1D. In one technique, the needle carries guidewire 130. In another embodiment, guidewire 130 is delivered through needle 110 during or following positioning of the needle.

Figure 2:
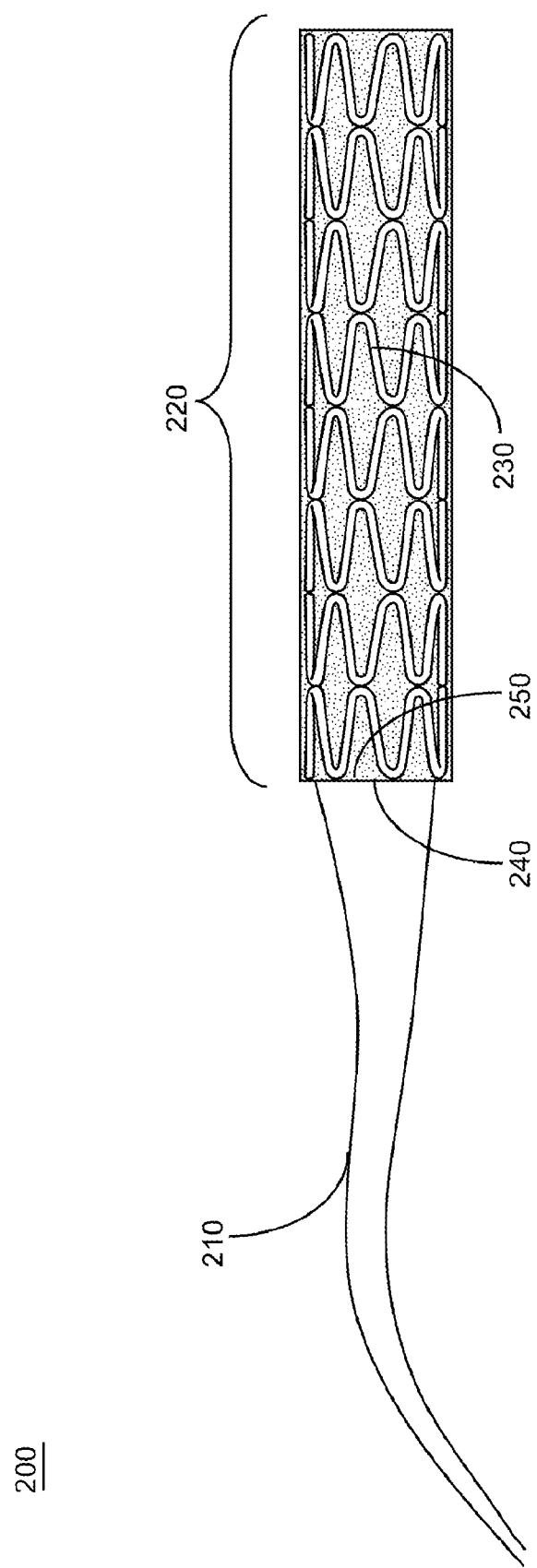
FIG. 2 is a view of one embodiment of a stent-graft assembly, in accordance with the present invention.

Catheter 105 may carry a stent graft and may be a system such as system 200 illustrated in FIG. 2. System 200 comprises a catheter 210 and a stent graft assembly 220 operably coupled to the catheter. The coupling of stent graft assembly 220 to catheter 210 comprises any known technique for securing a stent graft to a delivery catheter. In an example, the stent graft is crimped to the catheter, while in other examples, heat-sensitive adhesives are used. Stent graft assembly 220 includes a stent framework 230, an inner graft portion 240, and an outer graft portion 250. The stent graft assembly delivers a therapeutic agent, in one embodiment.

Figure 4D:
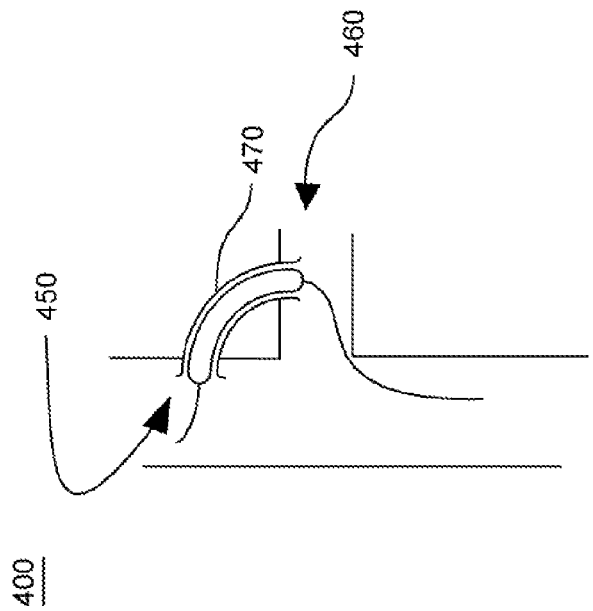

Catheter 210 may include a balloon to expand the stent graft as well as increase the size of a conduit or pathway (as illustrated in FIG. 4D below) to make it easier to pass the stent graft, or it may include a sheath that retracts to allow expansion of a self-expanding stent. Both types of catheter are well known in the art. Stent graft assembly 220 is shown coupled to catheter 210 for delivery within a vessel. The balloon may be any known balloon, and in some embodiments, the balloon is a cutting balloon, in the event the conduit left by the needle is too small to pass the stent graft system. Embodiments using a cutting balloon require that the stent graft assembly 220 is inserted only after the cutting balloon is removed from the area where deployment of the cutting balloon could impact upon deployment of the stent graft. Thus, embodiments using a cutting balloon may require operation of at least two balloons—a first cutting balloon to expand the pathway created by a needle, and a second balloon to expand the stent graft. Those of skill in the art will recognize that the balloon operable to expand the stent graft assembly could be replaced by a self-expanding stent, as known. Thus, the cutting balloon is expanded within the extravascular space to expand the pathway through the extravascular space and then the cutting balloon is removed from the pathway in the extravascular space prior to inserting the stent graft assembly into the expanded extravascular space. Further, in operation of the endovascular bypass disclosed herein, it may be desirable to operate an occluding device, such as an occluding balloon, above the site of the endovascular bypass to reduce bleed out.

One configuration is for stent framework 230 to be positioned between inner graft portion 240 and outer graft portion 250. Stent framework 230 may be made from a wide variety of medical implantable materials such as stainless steel, nitinol, tantalum, nickel, titanium, aluminum, polymeric materials, MP35N, stainless steel, titanium ASTM F63-83 Grade 1, niobium, high carat gold K 19-22, combinations of the above, and the like.

Inner graft portion 240 may be formed by applying a first polymer coating to a coating fixture having a flexible, non-stick surface. The polymer coating may comprise a material including, but not limited to, a biodurable polycarbonate-based aromatic or aliphatic urethane, other urethanes or polyurethanes, polylactide (PLA), poly-l-lactic acid (PLLA), polyglycolic acid (PGA) polymer, poly (e-caprolactone) (PCL), polyacrylates, polymethacrylates, polycaprolactone (PCL), polymethylmethacrylate (PMMA), combinations and/or copolymers of the above, and the like. The specific polymer, polymer combinations, or copolymers used may be adjusted as required by the specific needs of the medical device and the therapeutic agents delivered by the device.

Outer graft portion 250 may be formed by applying a second polymer coating that conjoins with inner graft portion 240 to encapsulate the stent framework. The inner and outer graft portions may comprise the same or different polymers. The two graft portions may conjoin by, for example, the second polymer coating adhering to the first polymer coating or by the second polymer coating melding with the first polymer coating to form a unitary structure. The stent framework is encapsulated, meaning fully enclosed, by the conjoined graft portions.

A therapeutic agent may be included in one, both, or neither of the graft portions. The inner and outer graft portions may include the same therapeutic agent, or inner graft portion 240 may include a first therapeutic agent, while outer graft portion 250 includes a second therapeutic agent.

Figure 3:
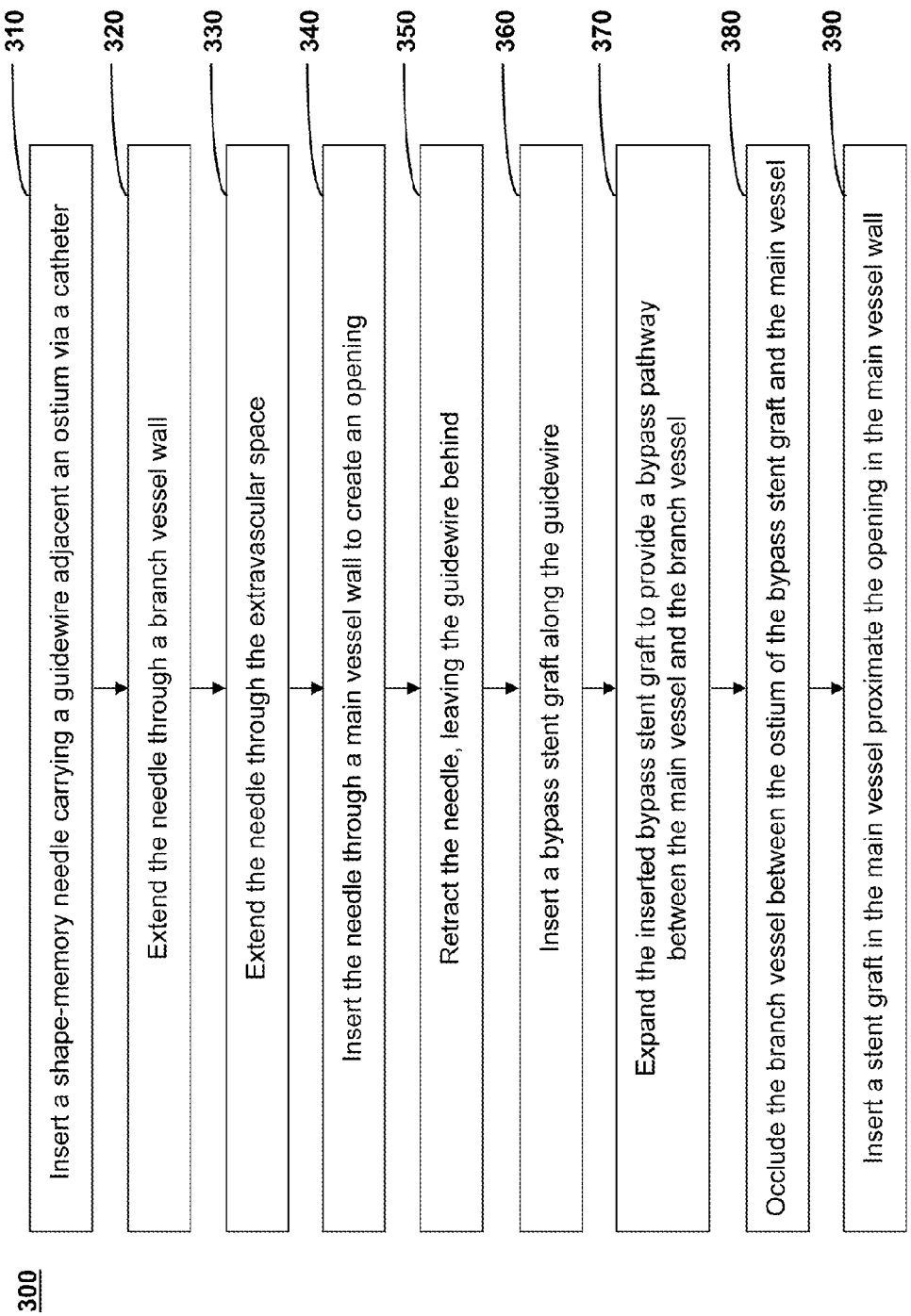
FIG. 3 is a flow chart illustrating the steps of a method for providing an endovascular bypass, in accordance with the present invention.

A flowchart of the steps of a method of providing an endovascular bypass between a main vessel and a branch vessel, in accordance with the present invention, is illustrated in FIG. 3 at 300.

At step 310, an elastic, e.g. shape-memory, needle is inserted in the vasculature adjacent an ostium via a catheter. The needle is hollow with the internal diameter sized to carry a guidewire within the needle. The guidewire is delivered through the needle during or following positioning of the needle. The inner diameter of the needle may be sized to fit as large a guidewire as possible to maximize the strength of the guidewire for inserting a stent or stent graft over the guidewire.

Endovascular approaches to the vasculature are known in the art and frequently involve threading a tubular device such as a catheter through the vasculature.

The term "main vessel" is defined broadly to encompass any vessel of the body other than a branch vessel (defined below). The main vessel may be any vessel of the body other than the branch vessel. In one embodiment, the main vessel is the aorta.

The term "branch vessel" is intended to identify the vessel with the ostium that will be occluded. However, use of these terms is not intended to limit the scope of the disclosure, and, instead, these terms are used to assist in an understanding of the disclosure. The term "branch vessel" as used herein is defined broadly as any vessel other than a main vessel, or a location of the same vessel other than the location called the main vessel. The term "branch vessel" is used in an effort to distinguish between the vessels, or locations of a single vessel, that form the ostium to be bypassed endovascularly. Any branch vessel may be used. In one embodiment, the branch vessel is a renal artery.

At step 320, the needle is extended through the branch vessel wall. In order to extend the needle through the branch vessel wall, the needle is extended through the sheath, as illustrated in FIGS. 1A, 1B, and 1C. Thus, during deployment of the needle, the needle is carried through the catheter with the needle restrained from its shape-memory, preset arc shaped, unconstrained configuration, positioned within the sheath. As the needle extends through the branch vessel wall, the needle extends through the extravascular space between the branch vessel and the main vessel, and at step 330, the needle extends through the extravascular space. During step 330, the needle creates a tunnel or passage through the extravascular space.

Prior to extending the needle through the branch vessel wall, an isolation device may be utilized to reduce the presence of blood in the area of the incision. An isolation device is known to those of skill in the art, including isolation devices with a vacuum pump to further clear the vessel of blood in the area where the incision will be made. In another example, an occluding balloon, as known in the art, may be deployed upstream from the incision site to reduce blood flow.

At step 340, the needle is inserted through a main vessel wall to create an opening. FIG. 4A illustrates the needle deployed through the sidewall of the branch vessel 460 and main vessel 450. The main vessel is located by known imaging techniques. After creating the opening through the main vessel, the needle retracts, leaving the guidewire, and in step 350, the needle is retracted from the main vessel, leaving the guidewire disposed within the vessel. The needle creates a bypass pathway or tunnel between the main and branch vessels. FIG. 4B illustrates the guidewire 465 disposed within the main vessel 450 and threaded through the extravascular space. Bleed out may be reduced with cautery devices, as known in the art.

Figure 4C:
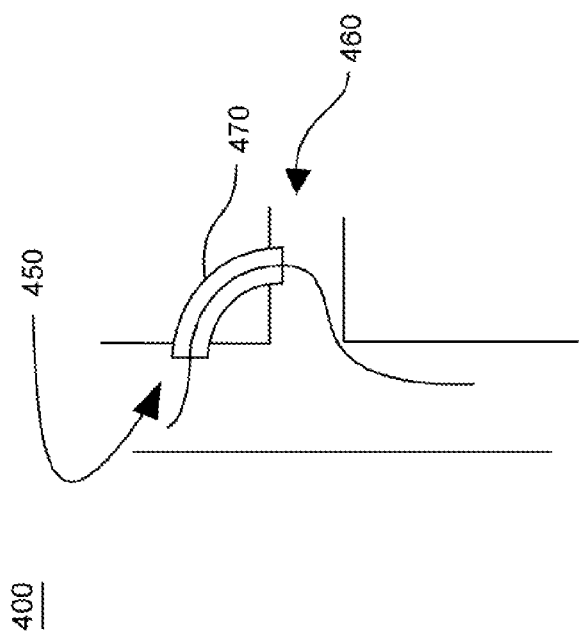

At step 360, a bypass stent graft is inserted along the guidewire to provide a pathway. FIG. 4C illustrates the bypass stent graft prior to deployment disposed within the bypass pathway or tunnel 470 in the extravascular space. In one embodiment, the bypass stent graft includes a balloon expansion device that is expanded within the bypass stent graft at step 370 to expand the inserted stent graft in the extravascular space, thereby creating a larger pathway. The bypass stent graft deployed in step 370 may be any appropriate stent graft device. For example, the bypass stent graft may be as illustrated in FIG. 2. It is possible that the balloon expansion device will be insufficient to expand the extravascular space, and a cutting balloon may be inserted to assist in expansion of the extravascular space.

FIG. 4D illustrates the bypass stent graft inflated within the bypass pathway or tunnel 470 in the extravascular space, with the balloon expansion device expanded within the bypass stent graft. In one technique, prior to inserting the bypass stent graft, a separate balloon expansion device is inserted over the guidewire to enlarge the extravascular path in the event that the conduit left by the needle is too small to insert the stent graft bypass. The balloon may be a cutting balloon, or the balloon may present a substantially smooth exterior surface. The balloon expansion device is removed prior to inserting the bypass stent graft over the guidewire.

The bypass stent graft can be configured with an oversized and flared end surface 515, as seen in FIG. 5A, configured so that blood pressure pushes the flared end surface against an interior surface of the vessel, creating a seal. In another embodiment, the bypass stent graft can be configured with at least one barbed surface 516 configured so that the barbed surface maintains the bypass stent graft in a position, as illustrated in FIG. 5B. In embodiments having a barbed surface, the barbed surface contributes to formation of a thrombus and may assist in formation of a seal between the surface of the bypass stent graft and the vessel wall. In another embodiment, a magnetic anastomosis device, e.g. a device available from Ventrica, Inc. of Fremont, Calif., is used to attach the bypass stent graft to the main and branch vessels. Magnetic anastomosis devices may be beneficial in reducing the number of sutures needed to reduce bleed out and secure the bypass stent graft. Magnetic anastomosis devices are self-seeking and self-aligning to connect blood vessels with their branches. In yet another example, the ends of the bypass stent graft are sutured to the vessel walls, using an endoluminal suturing device, as known to those of skill in the art.

Figure 4F:
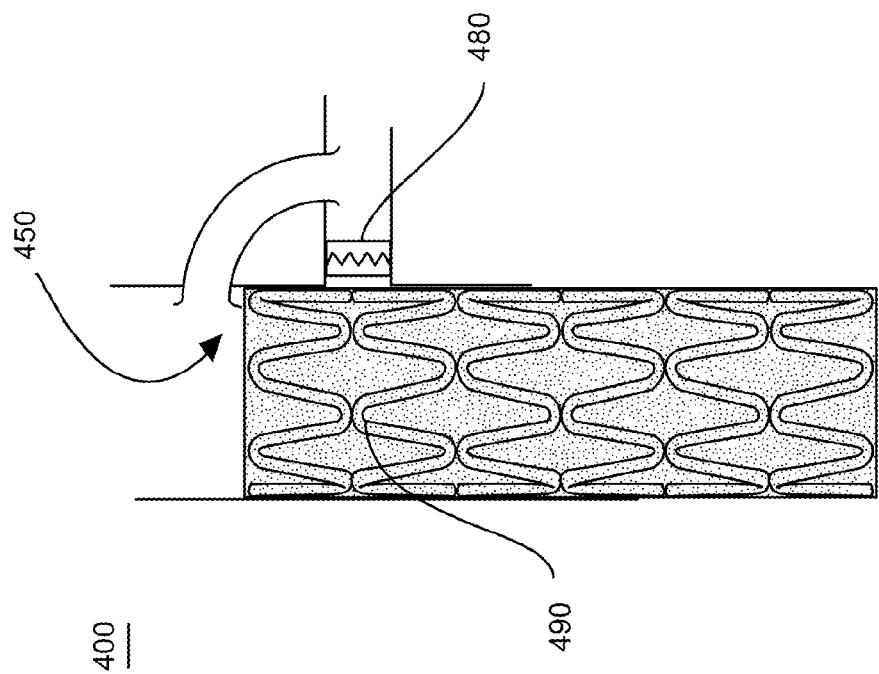
Figure 4E:
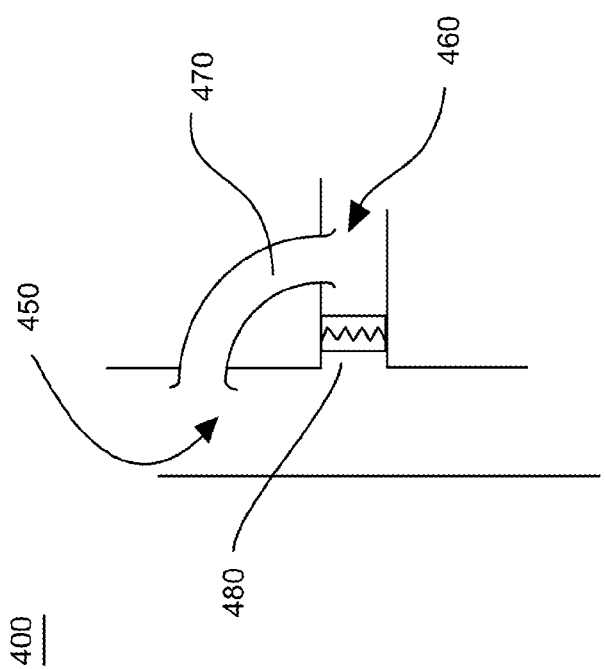

At step 380, the branch vessel is occluded between the ostium of the bypass stent graft in the branch vessel and the main vessel. FIG. 4E illustrates an occluding device 480 deployed in position in the branch vessel between the ostium of the bypass stent graft and the main vessel. An occluding device is known in the art.

This process is repeated for an opposing branch artery where there are two side branches, such as a renal artery.

At step 390, a main vessel stent graft is inserted in the main vessel proximate the opening created by the needle. FIG. 4F illustrates the main vessel stent graft 490 deployed in position within the main vessel. The main vessel stent graft may be any appropriate stent graft, such as, for example, the stent graft illustrated in FIG. 2.

Those of ordinary skill in the art will recognize that a bypass of the ostium between the main and branch vessels has been created with an endovascular approach. A bypass has been created, thus avoiding, for example, an ostial aneurysm, with blood flow maintained to the branch vessel via the bypass stent graft, and maintained through the main vessel via the main vessel stent graft.

Figure 6:
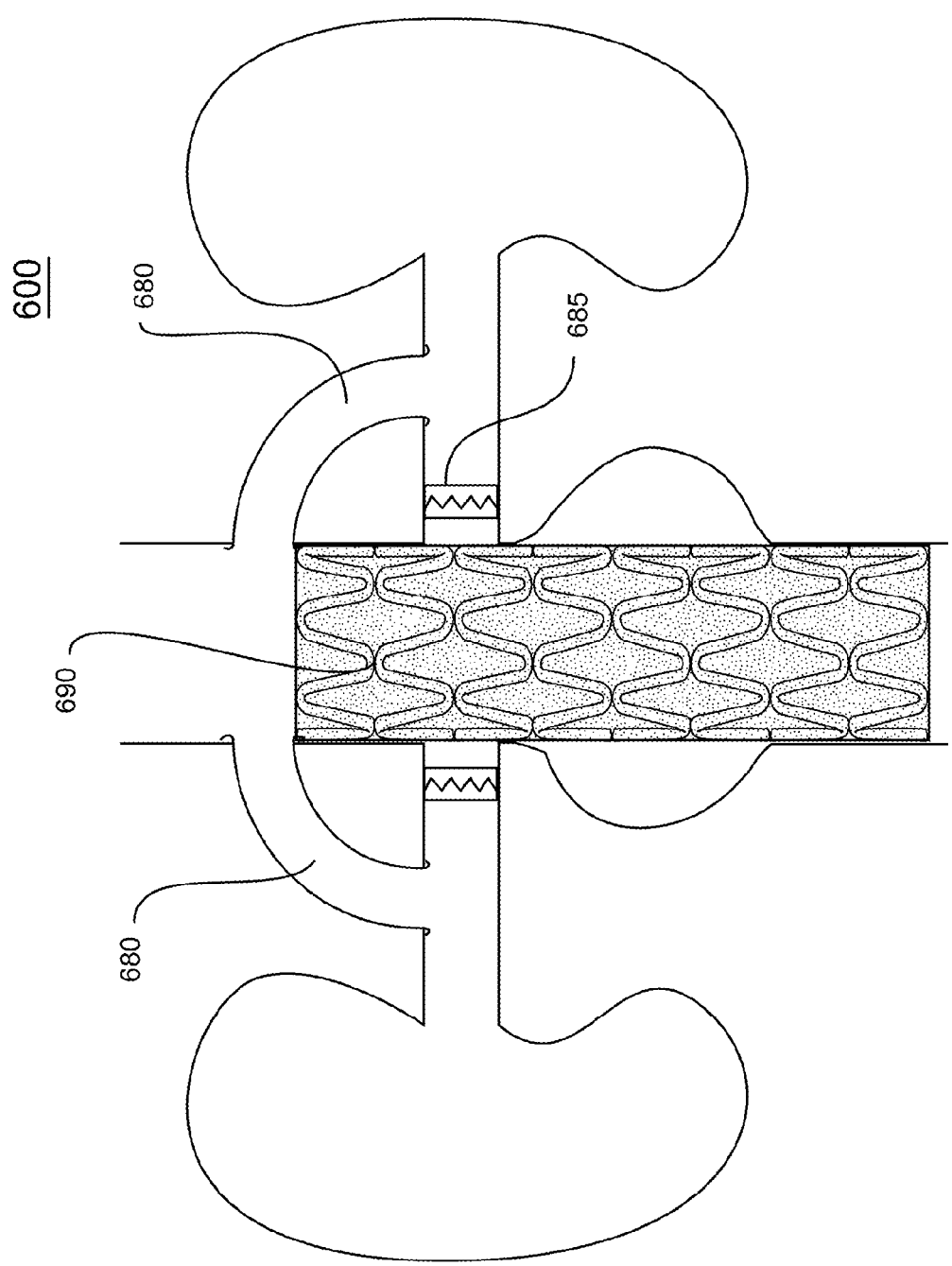
FIG. 6 is a schematic cross sectional view of a bypass of an ostium with a bypass stent graft and a main stent graft in accordance with one aspect of the present invention.

FIG. 6 illustrates a bypass of the ostium between the aorta and renal arteries. As illustrated in FIG. 6, stent graft 690 is in position, with bypass stent grafts 680 positioned between the aorta and renal arteries. Occluding devices 685 are positioned to occlude blood flow and prevent blood flow from the bypass stent grafts into the aortic aneurysm. The main stent graft is positioned adjacent the ostium and covering the renal artery such that the proximal end of the main stent graft is proximal the ostium and such that the distal end of the main stent graft is distal the ostium. The bypass stent graft perfuses at least one kidney via the expanded bypass stent graft.

Figure 7:
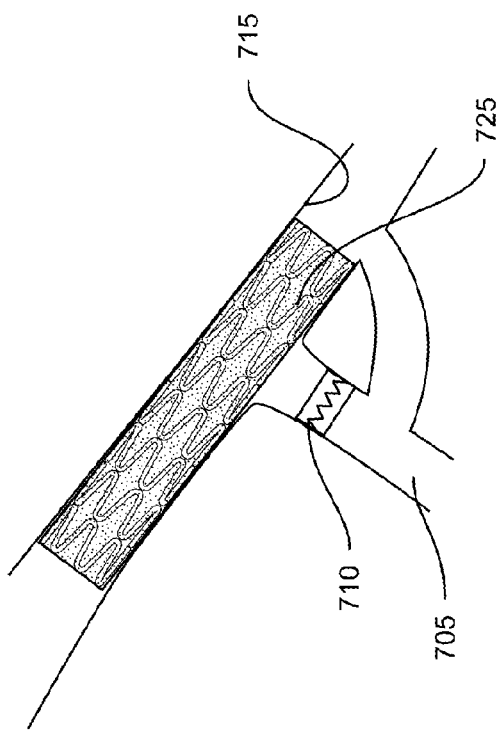
FIG. 7 is a schematic cross sectional view of a bypass of the ostium of the common iliac artery with the internal and external branches of the artery with a bypass stent graft and a main stent graft in accordance with the present invention.

FIG. 7 illustrates a bypass stent graft deployed at the ostium created at the intersection of the common iliac artery and the internal and external branches of the iliac artery. As shown in FIG. 7, the internal iliac branch 705 is occluded by an occluder 710, and the bypass stent graft 725 is deployed in the common iliac artery 715 and through the external iliac artery 725.

Figure 8:
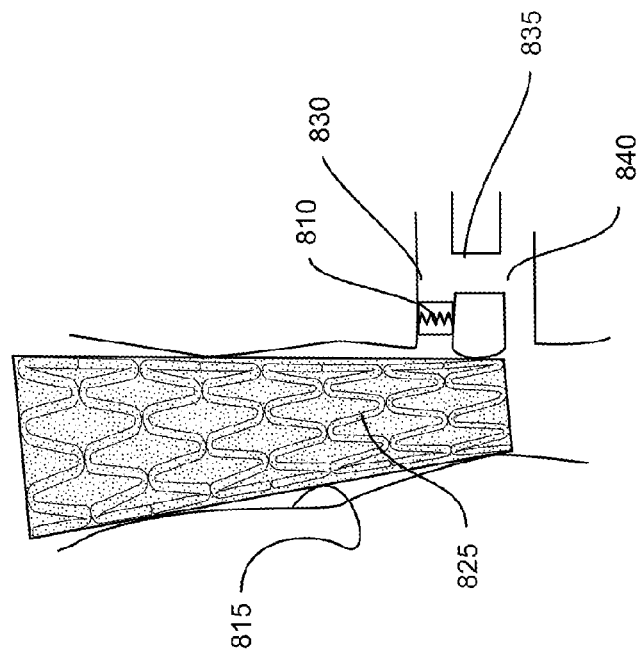
FIG. 8 is a schematic cross sectional view of a bypass of the ostium of the aorta with the celiac artery and superior mesenteric artery with a bypass stent graft and a main stent graft in accordance with the present invention.

FIG. 8 illustrates a bypass stent graft deployed at the ostium created at the intersection of the aorta and celiac and superior mesenteric arteries. As illustrated in FIG. 8, the celiac artery 830 is occluded with an occluder 810 with a bypass stent graft 835 extending from the celiac artery into the superior mesenteric artery 840. A main stent graft 825 is disposed in the aorta 815, so that blood flows through the main stent graft, into the superior mesenteric artery 840 and with blood flow through the bypass stent graft 835 into the celiac artery 830.

Figure 9C:
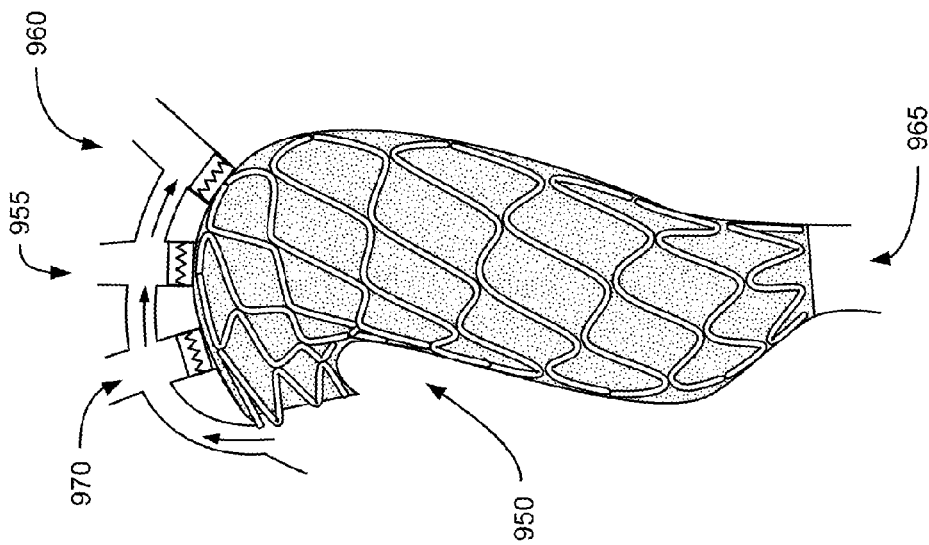
FIGS. 9A-9C are schematic cross sectional views of bypasses of arteries of the aortic arch with a bypass stent graft and a main stent graft in accordance with the present invention.
Figure 9B:
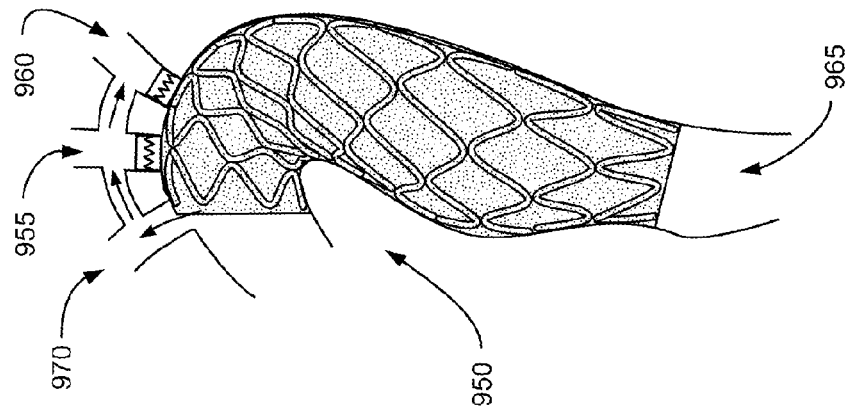
Figure 9A:
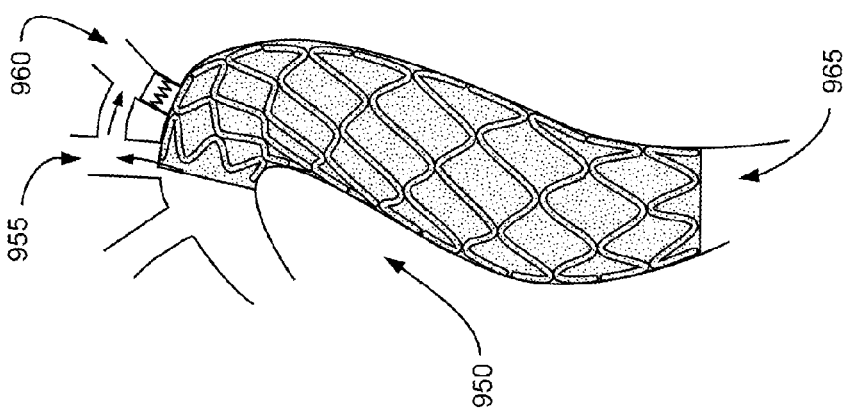

FIGS. 9A-9C illustrate additional embodiments of uses for the bypass stent graft. In FIG. 9A, the aortic arch 950 is illustrated with a bypass stent graft extending from the left carotid artery 955 to the left subclavian artery 960 with the left subclavian artery occluded, and a main stent graft 965 deployed within the aorta.

FIG. 9B illustrates an embodiment where the left carotid and left subclavian arteries are bypassed. A bypass stent graft extends from the brachian cephalic artery 970 to the left carotid artery 955, and another bypass stent graft extends from the left carotid artery 955 to the left subclavian artery 960. The left carotid and left subclavian arteries 955, 960 are occluded near their ostiums with the aorta, and a main stent graft 965 is deployed in the aorta.

FIG. 9C illustrates an embodiment where the brachian cephalic, left carotid, and left subclavian arteries 970, 955, 960 are bypassed near their ostiums with the aorta. A bypass stent graft extends from the aorta to the brachian cephalic artery 970, and the brachian cephalic artery 970 is occluded near its ostium with the aorta. Another bypass stent graft extends from the brachian cephalic artery 970 to the left carotid artery 955, with the left carotid artery 955 occluded near its ostium with the aorta. Yet another bypass stent graft extends from the left carotid artery 955 to the left subclavian artery 960, and the left subclavian artery 960 is occluded near its ostium with the aorta. A stent graft extends from the aortic-brachian cephalic bypass stent graft to beyond the occluded left subclavian artery.

A system for treating an ostial aneurysm includes a catheter and a retractable shape-memory needle carried within the catheter and covered with a sheath. In one embodiment, the needle is a hollow needle with the internal diameter sized to carry the guidewire within the needle. FIG. 1A illustrates the needle 110 carried within catheter 105, as well as sheath 120. The needle releasably carries a guidewire, as shown in FIG. 1B. When the needle is positioned adjacent an ostium in a branch vessel, as seen in FIG. 5A, the needle is extended to deploy the needle to a predetermined shape and puncture through a sidewall of the branch vessel, through the extravascular space, and through a sidewall of the main vessel. After deployment, the needle releases the guidewire and the needle is retracted to allow placement of a bypass stent graft in the extravascular space between the branch and main vessels.

Another embodiment according to the invention provides a system for treating a vascular condition and includes a catheter, stent graft, and a shape memory needle releasably carrying a guidewire disposed within the needle.

Stent grafts used herein comprise any appropriate, biocompatible material. In one example, the graft comprises polyester. In one example, the graft comprises venous material. In other embodiments, the graft comprises ePTFE, silicone, polyurethane, or any combination of the above. The stent graft may include a stent device, and the stent device may be coated with a therapeutic agent. The needle may be radio-opaque, and may be coated with a contrast material to augment radio-opacity. The stent comprises any appropriate material, such as stainless steel or nitinol. In other examples, the stent comprises tantalum, MP35N alloy, platinum, titanium, a chromium-based alloy, a suitable biocompatible alloy, a suitable biocompatible polymer, or combinations thereof.

The word "ostium" herein is the opening of a smaller branch into a larger main vessel. Locations "adjacent" an ostium are also to be construed broadly, such that activity at a location "adjacent" an ostium affects blood flow around the ostium. Therefore, for example, inserting a shape-memory needle adjacent an ostium via a catheter means placing the needle in a location wherein the needle placement affects blood flow around the ostium.

Additionally, it should be noted that a bypass could be obtained by inserting the bypass stent graft from the main vessel through the extravascular space and into the branch vessel. Such an approach may be slightly more difficult in practice, as targeting the branch vessel from the extravascular space will require greater precision as the branch vessel may have a smaller profile than the main vessel.

While the embodiments of the invention have been disclosed herein, various changes and modifications can be made without departing from the spirit and scope of the invention.

What is claimed is:

1. A method for fixing a stent graft, the method comprising:
 providing a main stent graft, the main stent graft including a proximal end and a distal end;
 providing a bypass stent graft;
 inserting an elastic needle adjacent an ostium formed by a renal artery and an aorta via a catheter;
 extending the needle through a wall of the renal artery;
 extending the needle through an extravascular space;
 inserting the needle through a wall of the aorta to create an opening;
 inserting a bypass stent graft through the extravascular space between the renal artery and the aorta;
 expanding the inserted bypass stent graft within the extravascular space;
 occluding the renal artery between the bypass stent graft and the aorta; and
 positioning the main stent graft adjacent the ostium, wherein the main stent graft is fixed in a position covering the renal artery such that the proximal end of the main stent graft is proximal the ostium and such that the distal end of the main stent graft is distal the ostium.

2. The method of claim 1 wherein the needle comprises a shape-memory material.

3. The method of claim 1 further comprising:
 operating a cutting balloon to expand the extravascular space; and
 removing the cutting balloon from the extravascular space prior to inserting the bypass stent graft into the extravascular space.

4. The method of claim 1 wherein at least one of the main stent graft and bypass stent graft is configured with an oversized and flared end surface configured so that blood pressure pushes the flared end surface against an interior surface of the vessel.

5. The method of claim 1 wherein at least one of the main stent graft and bypass stent graft is configured with at least one barbed surface configured so that the barbed surface maintains the stent graft in a position.

6. The method of claim 1 further comprising:
attaching the bypass stent graft to the renal artery and the aorta with a magnetic anastomosis device.

7. The method of claim 1 further comprising:
positioning the distal end of the main stent graft distal to an aneurysm.

8. A method for providing perfusion to at least one mammalian kidney, the method comprising:
providing a main stent graft, the main stent graft including a proximal end and a distal end;
providing a bypass stent graft;
inserting an elastic needle adjacent an ostium formed by a renal artery and an aorta via a catheter;
extending the needle through a wall of the renal artery;
extending the needle through an extravascular space;
inserting the needle through a wall of the aorta to create an opening;
inserting a bypass stent graft through the extravascular space between the renal artery and the aorta;
expanding the inserted bypass stent graft within the extravascular space;
occluding the renal artery between the bypass stent graft and the aorta;
positioning the main stent graft adjacent the ostium, wherein the main stent graft is fixed in a position covering the renal artery such that the proximal end of the main stent graft is proximal the ostium and such that the distal end of the main stent graft is distal the ostium; and
perfusing at least one kidney via the expanded bypass stent graft.

9. The method of claim 8 further comprising:
operating a cutting balloon to expand the extravascular space; and
removing the cutting balloon from the extravascular space prior to inserting the bypass stent graft into the extravascular space.

10. The method of claim 9 further comprising:
attaching the bypass stent graft to the renal artery and the aorta with a magnetic anastomosis device.

11. A method for fixing a stent graft, the method comprising:
providing a main stent graft, the main stent graft including a proximal end and a distal end;
providing a bypass stent graft;
locating at least one aneurysm near an ostium formed by a main vessel and a branch vessel;
inserting a bypass stent graft through a wall of the branch vessel and then through a wall of the main vessel;
fixing the main stent graft such that the proximal end is fixed on a first side of the aneurysm and ostium and the distal end of the main stent graft is fixed on a second side of the ostium and aneurysm, such that the main stent graft covers the ostium and aneurysm.

12. The method of claim 11 wherein inserting the bypass stent graft through a wall of the branch vessel and then through a wall of the main vessel comprises inserting an elastic needle through the wall of the branch vessel, through an extravascular space, and then through the wall of the main vessel.

13. The method of claim 12 wherein the elastic needle is delivered via a delivery catheter.

14. The method of claim 11 wherein the bypass stent graft and main stent graft are delivered via a delivery catheter.

15. The method of claim 11 wherein at least one of the main stent graft and bypass stent graft includes an oversized and flared end surface configured so that blood pressure pushes the flared end surface against an interior surface of the vessel.

16. The method of claim 11 wherein at least one of the main stent graft and bypass stent graft is configured with at least one barbed surface configured so that the barbed surface maintains the stent graft in a position.

17. The method of claim 11 wherein inserting a bypass stent graft through a wall of the branch vessel and then through a wall of the main vessel comprises:
delivering an elastic needle to the branch vessel, wherein the elastic needle carries a guidewire;
extending the elastic needle through the wall of the branch vessel and into an extravascular space;
creating a tunnel through the extravascular space responsive to the extension of the elastic needle;
extending the elastic needle through the wall of the main vessel based on the creation of the tunnel;
retracting elastic needle based on the extension through the wall of the main vessel;
leaving the guidewire in the vessel based on the retraction;
delivering a bypass stent graft along the guidewire.

* * * * *